US009170256B2

(12) United States Patent
Ding et al.

(10) Patent No.: US 9,170,256 B2
(45) Date of Patent: Oct. 27, 2015

(54) DEVICE AND METHOD FOR ERYTHROCYTE MORPHOLOGY ANALYSIS

(75) Inventors: Jianwen Ding, Hunan (CN); Fengliang Zhou, Hunan (CN); Guangming Liang, Hunan (CN)

(73) Assignee: AVE SCIENCE & TECHNOLOGY CO., LTD (CN)

( * ) Notice: Subject to any disclaimer, the term of this patent is extended or adjusted under 35 U.S.C. 154(b) by 0 days.

(21) Appl. No.: 13/880,593

(22) PCT Filed: Sep. 16, 2011

(86) PCT No.: PCT/CN2011/079710
§ 371 (c)(1),
(2), (4) Date: Apr. 19, 2013

(87) PCT Pub. No.: WO2013/037119
PCT Pub. Date: Mar. 21, 2013

(65) Prior Publication Data
US 2014/0185906 A1 Jul. 3, 2014

(51) Int. Cl.
G06K 9/00 (2006.01)
G01N 33/50 (2006.01)
G01N 33/49 (2006.01)
G01N 15/14 (2006.01)
G01N 15/00 (2006.01)

(52) U.S. Cl.
CPC ........ *G01N 33/5091* (2013.01); *G01N 15/1475* (2013.01); *G01N 33/49* (2013.01);
(Continued)

(58) Field of Classification Search
None
See application file for complete search history.

(56) References Cited

U.S. PATENT DOCUMENTS 4,129,854 A * 12/1978 Suzuki et al. .................. 382/134
4,965,725 A * 10/1990 Rutenberg .................... 382/224
(Continued)

FOREIGN PATENT DOCUMENTS

CN 1037035 A 11/1989
CN 1383522 A 12/2002
(Continued)

OTHER PUBLICATIONS

International Search Report for corresponding application No. PCT/CN2011/079710 filed Sep. 16, 2011; Mail date Jun. 28, 2012.

*Primary Examiner* — Tsung-Yin Tsai
(74) *Attorney, Agent, or Firm* — Cantor Colburn LLP

(57) ABSTRACT

The disclosure provides a device and a method for performing morphological analysis for erythrocytes, wherein the method for performing morphological analysis for erythrocytes comprises: collecting a morphological image of each of cells in a sample through a Charge Coupled Device (CCD) after amplifying the sample through an automatic microscope; segmenting and positioning the image and extracting target feature parameters after digitizing the image through an image-digital converter; isolating morphological feature parameters of each of the erythrocytes through a classifier established on the basis of the neural network, and normalizing each type of the morphological feature parameters of the erythrocytes through a feature fusion device established on the basis of fuzzy clustering; performing a statistical analysis on each type of normalized parameters obtained or performing a comprehensive statistical analysis according to a plurality of types of parameters, and expressing the result of the statistical analysis or the comprehensive statistical analysis in the form of graph or numerical table, thereby judging whether the morphology of the erythrocyte is normal. The source and property of the erythrocytes can be identified according to the detection for each type of the erythrocytes with the abnormal morphology.

11 Claims, 13 Drawing Sheets

(52) U.S. Cl.
CPC ......... *G06K 9/0014* (2013.01); *G06K 9/00147* (2013.01); *G01N 2015/0069* (2013.01); *G01N 2015/1493* (2013.01); *G01N 2015/1497* (2013.01)

(56) References Cited

U.S. PATENT DOCUMENTS

| | | | |
|---|---|---|---|
| 5,828,776 A | * | 10/1998 | Lee et al. ................. 382/133 |
| 7,268,939 B1 | * | 9/2007 | McDowell ................. 359/368 |
| 2013/0094750 A1 | * | 4/2013 | Tasdizen et al. ............. 382/134 |

FOREIGN PATENT DOCUMENTS

| | | |
|---|---|---|
| CN | 101713776 A | 5/2010 |
| CN | 102359938 A | 2/2012 |
| EP | 0575091 A1 | 12/1993 |
| WO | 9120048 A1 | 12/1991 |

\* cited by examiner

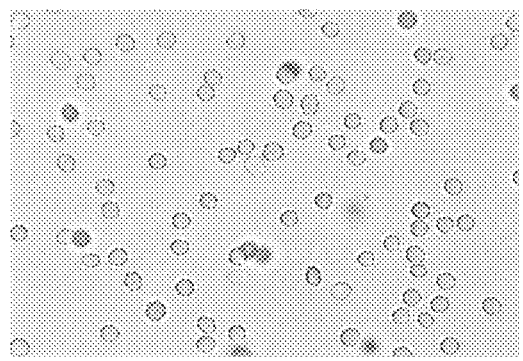
Fig. 5
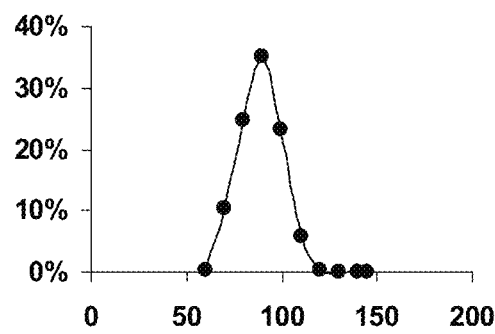
Fig. 6.1
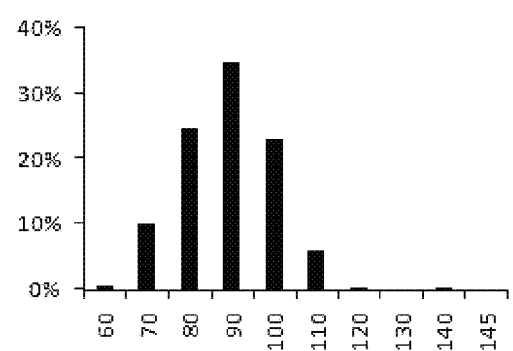
Fig. 6.2
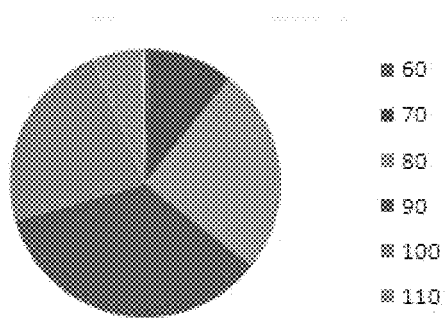
Fig. 6.3
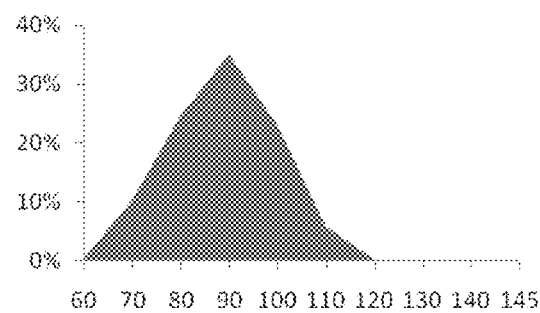
Fig. 6.4

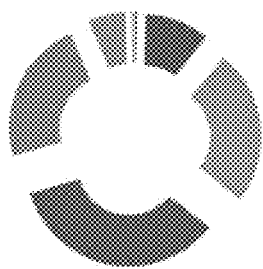
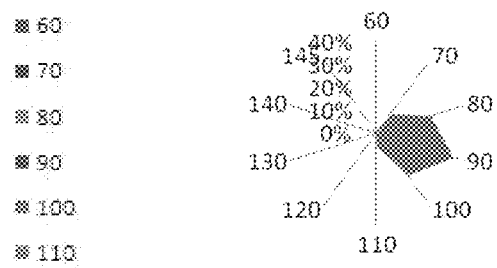
Fig. 6.5　　　　　　　　　　　Fig. 6.6
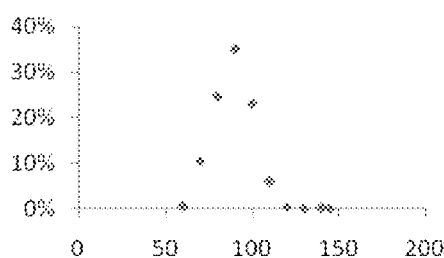
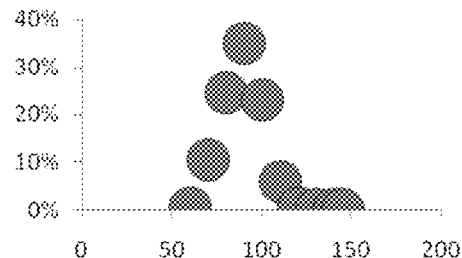
Fig. 6.7　　　　　　　　　　　Fig. 6.8
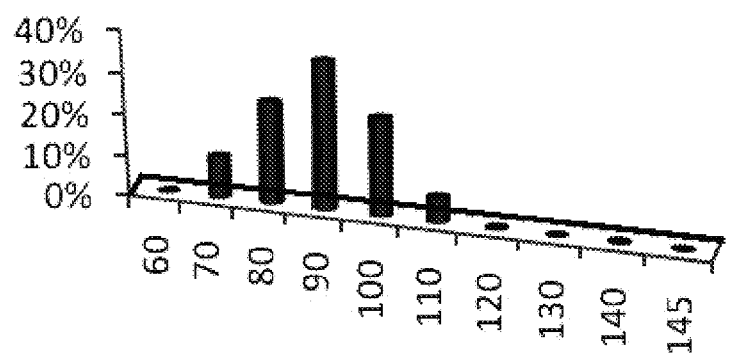
Fig. 6.9

DEVICE AND METHOD FOR ERYTHROCYTE MORPHOLOGY ANALYSIS

TECHNICAL FIELD OF THE INVENTION

The disclosure relates to a device and a method for performing morphological analysis for erythrocytes in a sample, and in particular to a device and a method for performing morphological analysis for erythrocytes, which is able to automatically identify the type and source of the erythrocytes contained in the sample.

BACKGROUND OF THE INVENTION

People have begun to work on a method for counting erythrocytes as early as in 1852, and a counting plate for counting erythrocytes was invented in 1855. An American scientist named W. H. Coulter proposed in 1947 a patent technology which counts particles using a resistance method, and this technology was successfully applied to count the erythrocytes in 1956. With the fast change of science and technology, various ways for detecting the number of erythrocytes emerge constantly. At present, the research and development means applied mainly includes: capacitive mode, photoelectric mode and laser mode, centrifugal mode, resistance mode and a combination of each mode. So far, many countries have begun to produce various types of erythrocyte analyzers; after half a century of development, above analyzer has achieved a very significant improvement. The classification of the erythrocytes becomes refined and the counting becomes more and more precise. However, erythrocyte parameters of the existing erythrocyte morphological analysis are obtained through calculating the mean value. For example, morphological classification parameters used for the anaemia, such as Mean Corpuscular Volume (MCV), Mean Corpuscular haemoglobin (MCH) and Mean Corpuscular haemoglobin Concentration (MCHC), are all calculated according to erythrocyte quantity, haemoglobin concentration and hematocrit value, but are not actually measured values; therefore, the measured data of the erythrocyte quantity, the haemoglobin content and the hematocrit value must be accurate, otherwise, the obtained morphological classification parameters would have great errors.

The artificial microscopy (or called as manual microscopic examination) is a classical detection method, which manually measures the diameter of each erythrocyte through a micrometer on an eyepiece of a microscope and then analyzes the data for judgement. However, the method of the artificial microscopy causes a heavy workload for workers, and the error judgment can be easily caused due to fatigue, and patient's diagnosis may be delayed due to low working efficiency and slow working speed.

Therefore, how to make erythrocyte counting quicker, more accurate and more cost-effective is the problem confronted in clinical examination in hospitals at present.

SUMMARY OF THE INVENTION

The technical problem to be solved by the disclosure is to provide, in view of the disadvantages in the conventional art, a device and a method for performing morphological analysis for erythrocytes, which uses morphological feature parameters and a neural network to perform statistical expression for the source and property of the erythrocytes in a sample, so as to make relevant staffs refer to it and judge whether the morphology of the erythrocytes is normal, and thus make the assist for identifying the source and property of the erythrocytes.

In order to solve the technical problem above, the technical scheme adopted by the disclosure is to provide a device for performing morphological analysis for erythrocytes, comprising:

a. an automatic microscope, wherein a low-power objective lens of the automatic microscope is configured to scan a sample in a set area and to mark a found target area, and meanwhile a high-power objective lens of the automatic microscope is configured to scan the marked area;

b. a camera or a Charge Coupled Device (CCD) element, which is configured to collect information of a image of the marked area;

c. an image-digital converter for analyzing and processing the image, wherein the image-digital converter is configured to segment and position cells contained in the image collected at first, and then to digitize the segmented image to extract four types, including size, shape, chromaticity and texture, of morphological feature parameters of each of the cells;

d. a classifier established on the basis of a neural network, wherein the classifier is configured to classify the cells according to the four types, including size, shape, chromaticity and texture, of the morphological feature parameters of each of the cells, in the above step, so as to isolate erythrocytes from each type of the cells;

e. a feature fusion device established on the basis of fuzzy clustering, wherein the feature fusion device is configured to perform normalized dimension reduction on the four types, including size, shape, chromaticity and texture, of multi-dimensional morphological feature parameters of the erythrocytes, which are isolated in the above step, to obtain four feature values of size, shape, chromaticity and texture, and then to perform statistical calculation and statistical graphic expression respectively according to size, shape, chromaticity and texture features of all erythrocytes in a specimen to provide real objective basis for analyzing type and source of the erythrocytes in the sample;

f. an output apparatus, which is configured to intuitively display a detection result; and g. a control unit, which is connected to the automatic microscope, the camera or CCD element, the image-digital converter and the output apparatus respectively to control actions of the automatic microscope, the camera or CCD element, the image-digital converter and the output apparatus.

The output apparatus expresses data combination of feature parameters, which represent colour gradient and texture of a central area of the erythrocytes, owned by each type of the erythrocytes, and a method for analyzing and identifying the erythrocytes in the sample comprises determining the source or type of the erythrocytes in the sample according to feature change in the central area of the erythrocytes.

A method for performing morphological analysis for the erythrocytes in the sample comprises: performing identification and classification counting by referring to different morphological feature parameter data of each type of erythrocytes clinically confirmed and representing different meanings, and then performing statistical processing according to the proportion of a data combination of a morphological feature parameter of the morphological feature parameters of each type of erythrocytes to a data combination of the same morphological feature parameter of the morphological feature parameters of total erythrocytes in the sample and finally to perform expression in the form of graph or data.

As an analysis method and a detection means, comprehensively analyzing a combination of more than two types of morphological feature parameters of each type of the erythrocytes in the sample according to a statistical method to obtain a multi-parameter analysis result of each type of the erythrocytes in the sample, and determining the morphological change of the erythrocytes according to the change of the parameter and intuitively expressing the type of the morphological change of the erythrocytes in the sample through graph and data.

One same result presented by using the device to analyze erythrocytes has different clinical meanings in different kind of samples, if erythrocytes with small volume and low pigment appear in a sample, the result analyzed by the device is that a single erythrocyte has a small volume and a low chromaticity, and for total erythrocytes morphological feature parameters, a morphological analysis graph, which takes a parameter combination representing size as a horizontal coordinate and takes feature parameter data representing chromaticity as a longitudinal coordinate, is adopted to express left shift of the width of the erythrocyte distribution increases and the erythrocyte distribution shifts left, the area of the erythrocyte distribution shifts downwardly, that is, the total erythrocytes morphological feature parameters are expressed as an erythrocyte morphological distribution chart with dispersion toward left and descending downwardly, wherein a type of anaemia is prompted if this type of the graph appears in a blood sample, whereas it means the erythrocytes in the sample come from renal erythrocytes if this type of the graph appears in a urine sample and occupies a certain proportion; if erythrocytes with large volume and high pigment appear in a sample, the result analyzed by the device is that a single erythrocyte has a large volume and a high chromaticity, and for total erythrocytes morphological feature parameters, a morphological analysis graph, which takes a parameter combination representing size as a horizontal coordinate and takes feature parameter data representing chromaticity as a longitudinal coordinate, is adopted to express that the width of an erythrocyte distribution increases and the erythrocyte distribution shifts right and an area of the erythrocyte distribution shifts upwardly, that is, the total erythrocytes morphological feature parameters is expressed as an erythrocyte morphological distribution chart with dispersion toward right and ascending upwardly, wherein another type of anaemia is prompted if this type of the graph appears in a blood sample, whereas it means that the erythrocytes in the sample come from non-renal erythrocytes if this type of the graph appears in a urine sample and occupies a certain proportion.

The disclosure also provides a method for performing morphological analysis for erythrocytes, comprising the following steps:

Step 1: scanning a sample in a set area and marking a found target area through a low-power objective lens of an automatic microscope and meanwhile scanning the sample in the marked area through a high-power objective lens of the automatic microscope;

Step 2: collecting information of an image of the sample in the marked area through a camera or a CCD element;

Step 3: segmenting and positioning cells contained in the image collected and then digitizing the segmented image to extract morphological feature parameters of each of the cells through an image-digital converter, wherein four types of features including size, shape, chromaticity and texture are used to describe each of the cells;

Step 4: inputting the four types, including size, shape, chromaticity and texture, of the morphological feature parameters of each of the cells, which are obtained in the above step, into a classifier established on the basis of a neural network, and then isolating erythrocytes from each type of the cells;

Step 5: inputting the four types, including size, shape, chromaticity and texture, of the morphological feature parameters of the erythrocytes, which are isolated in the Step 4, into a feature fusion device established on the basis of fuzzy clustering, and then normalizing each type of multi-dimensional morphological feature parameters by the feature fusion device to obtain a one-dimensional feature vector; and Step 6: displaying each type of normalized feature values of all erythrocytes in each specimen through an outputting apparatus to obtain a statistical graph of each type of normalized feature parameters.

The above morphological analysis method for erythrocytes further includes Step 7: performing statistical processing according to the proportion of each type of the erythrocytes to total of the erythrocytes in the sample and performing expression in the form of graph or data to analyze and identify the erythrocytes in the sample.

The method for performing morphological analysis for erythrocytes further includes Step 8: for each type of normalized morphological feature vectors, through giving a feature value threshold, calculating the proportion of a data combination of one morphological feature parameter of the morphological feature parameters of the erythrocytes whose the normalized morphological feature vectors are higher or lower than the threshold to a data combination of the same morphological feature parameter of the morphological feature parameters of total erythrocytes in the sample, and performing expression in the form of graph or data after performing statistical processing so as to provide objective basis for the analysis and identification of the erythrocytes in the sample.

The classifier established on the basis of the neural network includes a feedback process which is to refine, classify and compensate feature parameters for a suspected object and a wrongly identified object that are classified out, and to establish a corresponding mathematical model to train the neural network, wherein the neural network automatically learns and memorizes these refined, classified and compensated feature parameters into a model database, and then to return to the classifier based on the neural network to classify the cells.

The normalized size feature vector obtained in Step 6 expresses data combination of feature parameters, representing size, owned by each type of the erythrocytes; the method for analyzing and identifying the erythrocytes in the sample determines the source or type of the erythrocytes in the sample according to direction and degree of deviation obtained by comparing the size distribution of the erythrocytes with the size distribution of normal erythrocytes.

The normalized shape feature vector obtained in Step 6 expresses data combination of feature parameters, representing shape, owned by each type of the erythrocytes; the method for analyzing and identifying the erythrocytes in the sample determines the source or type of the erythrocytes in the sample according to the change of the erythrocyte shape feature parameter.

The normalized chromaticity feature vector obtained in Step 6 expresses data combination of feature parameters, representing chromaticity, owned by each type of the erythrocytes; the method for analyzing and identifying the erythrocytes in the sample determines the source or type of the erythrocytes in the sample according to direction and degree of deviation obtained by comparing the erythrocyte chromaticity with normal erythrocyte chromaticity.

The normalized texture feature vector obtained in Step 6 expresses a data combination of feature parameters, representing texture, owned by each type of the erythrocytes; the method for analyzing and identifying the erythrocytes in the sample determines the source or type of the erythrocytes in the sample according to the change of the erythrocyte texture feature parameter.

Any one of above method for performing morphological analysis for erythrocytes is adopted separately or at least two of above method for performing morphological analysis for erythrocytes are adopted comprehensively for the analysis and identification of the erythrocytes in the sample.

Compared with the conventional art, the disclosure has advantages as follows: the disclosure collects morphological images of each of cells in a sample (blood, urine) through a CCD after amplifying the sample through an automatic microscope, obtains morphologic feature parameters of each of cells after digital image processing, inputs the parameter into a classifier established on the basis of the neural network to isolate the erythrocytes, normalizes each type of the morphological feature parameters of the erythrocytes through a feature fusion device established on the basis of fuzzy clustering, performs a statistical analysis on each type of normalized parameters obtained or performs a comprehensive statistical analysis according to a plurality of types of parameters, and expresses the result in the form of graph or numerical table, thereby judging whether the morphology of the erythrocyte is normal. The source and property of the erythrocytes can be identified according to the detection for each type of the erythrocytes with the abnormal morphology.

By taking that the software may have an error for identifying particular objects into account on the basis of existing urine cell identification, the disclosure introduces morphological parameters and the statistical analysis method thereof; with this method, the device can automatically analyze the source of the erythrocytes in a blood sample and/or a urine sample according to the statistical analysis of all target parameters in the sample. Since this method performs statistical judgment by adopting all objects in the sample, the impact from an error which is caused by wrong identification for particular objects is reduced. The disclosure is an application innovation of the statistical method in aspect of analysing the morphological parameters of urine erythrocytes.

BRIEF DESCRIPTION OF THE DRAWINGS

FIG. 5 is an image of normal erythrocytes photographed by a digital CCD;

FIG. 6.1 is a statistical curve chart of the size feature parameter of normal erythrocytes, of which the distribution width meets a<L and the peak value b is in a normal range, namely, D1<b<D2;

FIG. 6.2 to FIG. 6.9 are other expressions of FIG. 6.1;

DETAILED DESCRIPTION OF THE EMBODIMENTS

Figure 1:
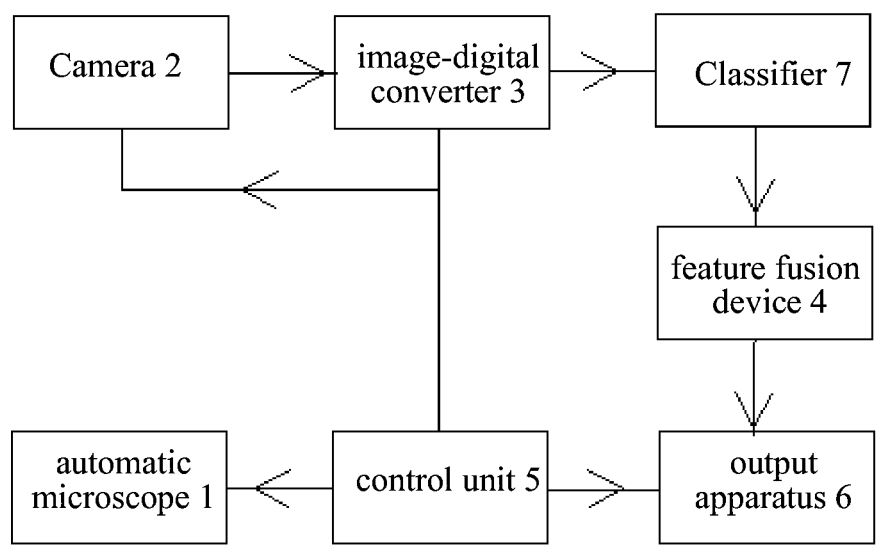
FIG. 1 is a structure diagram of a device for performing morphological analysis for erythrocytes according to the disclosure.

FIG. 1 is a schematic diagram of a device for performing morphological analysis for erythrocytes according to the disclosure. As shown in FIG. 1, the device for performing morphological analysis for erythrocytes according to the disclosure comprises:

a. an automatic microscope 1, of which a low-power objective lens is configured to scan a sample (or samples) in a set area at first and to mark a found target area, and meanwhile of which a high-power objective lens is configured to scan the sample(s) in the marked area;

b. a camera or a CCD element 2, which is configured to collect information of an image of the sample(s) in the marked area;

c. an image-digital converter 3 for generating digital expression of the image above, wherein the image-digital converter 3 is configured to segment and position cells contained in the image collected at first, and then to digitize the segmented image to extract four types of morphological feature parameters of each of the cells, including size, shape, chromaticity and texture;

d. a classifier established on the basis of a neural network, wherein the classifier is configured to isolate erythrocytes from each type of cells according to the four types of the morphological feature parameters of each of the cells, including size, shape, chromaticity and texture, which are obtained in the above step;

e. a feature fusion device 4 established on the basis of fuzzy clustering, wherein the feature fusion device 4 is configured to normalize each type of multi-dimensional morphological feature parameters obtained in the above step to provide basis for the statistics and classification of the erythrocytes;

f. an output apparatus 6, which can comprise a monitor and a printer and is configured to intuitively display a detection result; and g. a control unit 5, which is connected to the automatic microscope 1, the camera or CCD element 2, the image-digital converter 3 and the output apparatus 6 respectively to control the action of the automatic microscope 1, the camera or CCD element 2, the image-digital converter 3 and the output apparatus 6.

In this embodiment, the neural network adopted in the classifier 7 is a Back Propagation (BP) three-layer neural network based on RDROP algorithm, wherein the three-layer neural network includes an input layer, an output layer and a hidden middle layer. Further, the data of the neural network can be expandable and has a feature of self-memorability. The neural network is used for expert system training and sample target identification. Of course, this classifier also can adopt other types of neural networks.

For the neural network, there have been a lot of materials describing it in detail, thus no further description is needed here.

The neural network of the disclosure has many input nodes, each of which expresses a certain morphological feature parameter of cells to be measured, wherein the method of extracting the morphological feature parameters and the classification state of the morphological feature parameters are described as follows:

1. Feature Extraction Method

First, an expert manually classifies visible ingredients in sample images according to morphological features of erythrocytes and hereby establishes a classification semantic model and then establishes a classification mathematic model on that basis, so as to define various morphological features of the erythrocytes, wherein there are totally four types of the features, including size feature, shape feature, chromaticity feature and texture feature.

2. Feature Classification

The disclosure extracts over 100 dimensional target features, and the following is only the description of representative features:

2.1 Size feature, including area, circumference, equivalent diameter, long axis, short axis, mean radius and the like;

2.2 Shape feature, which is used to describe the shape of targets, mainly including 26 features such as circle ratio, eccentricity, centre of gravity of area, curvature, feature related to area chord distribution morphology descriptor, boundary fitting polygon morphology descriptor, Fourier coefficient morphology description feature vector, feature related to morphology description based on convex hull, feature description based on bounding rectangle, shape feature description based on constant distance feature, and shape feature extracted based on area skeleton, wherein a plurality of above types of the features, such as the feature related to area chord distribution morphology descriptor, the feature related to morphology description based on convex hull, the feature description based on bounding rectangle, shape feature description based on constant distance feature, and shape feature extracted based on area skeleton are new methods for describing the morphology provided by the disclosure.

2.3 Chromaticity feature, including target area colour histogram based on HSV (Hue, Saturation, Value), area target main-colour feature extraction based on probability window, and colour distance.

2.4 Texture feature, which is a multi-scale texture feature based on wavelet transform domain, including: multi-scale wavelet energy proportion, multi-scale wavelet standard deviation, texture feature of comprehensive co-occurrence matrix, texture spectrum fused Zernike moment feature description.

Figure 2:
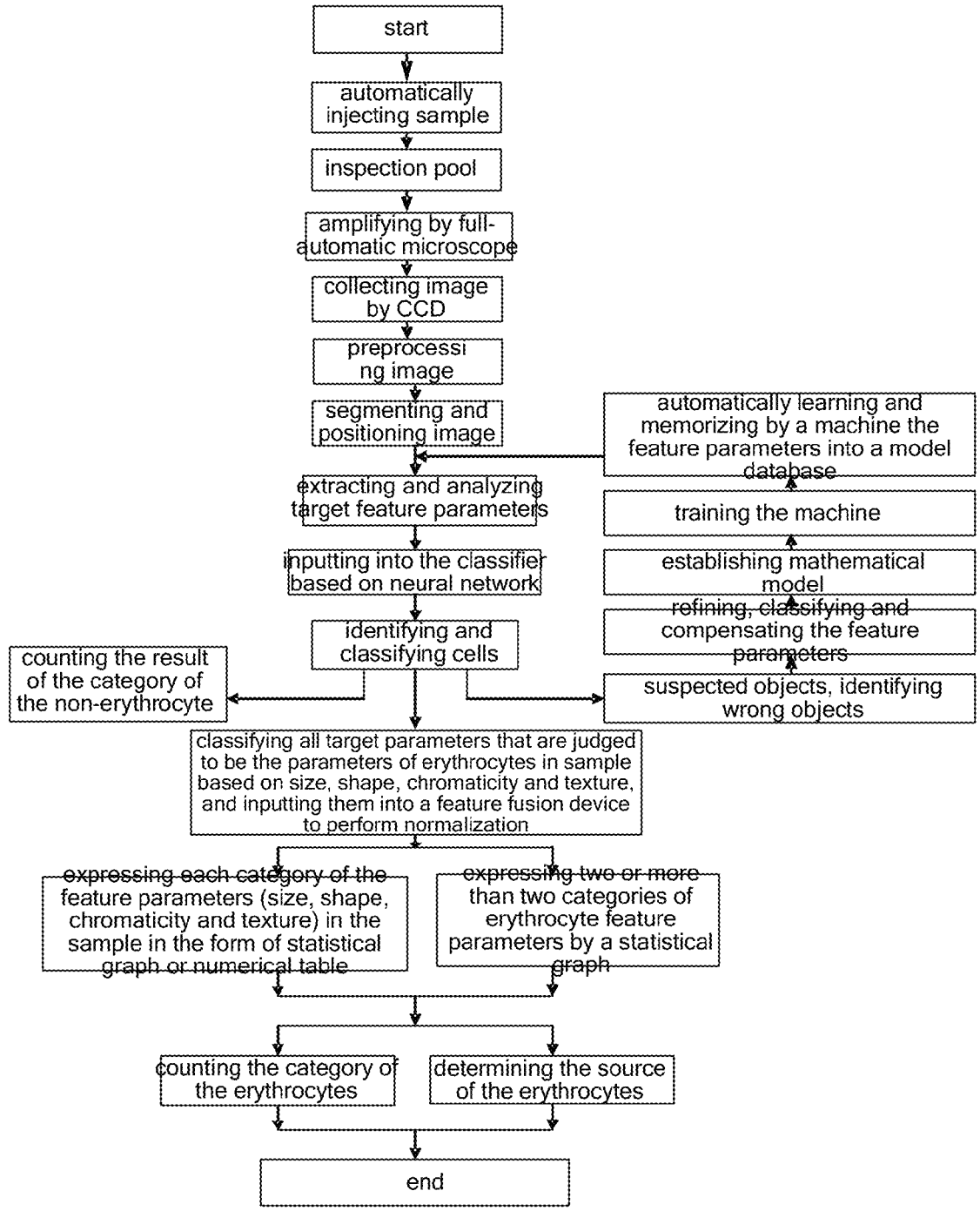
FIG. 2 is an operational flow diagram of a method for performing morphological analysis for erythrocytes according to the disclosure.

Specifically, as shown in FIG. 2, the operation steps of the method for performing morphological analysis for erythrocytes are as follows:

Step 1: scanning a sample (or samples) in a set area through a low-power objective lens of an automatic microscope 1, marking a found target area and meanwhile scanning the marked area through a high-power objective lens of the automatic microscope 1.

Figure 11:
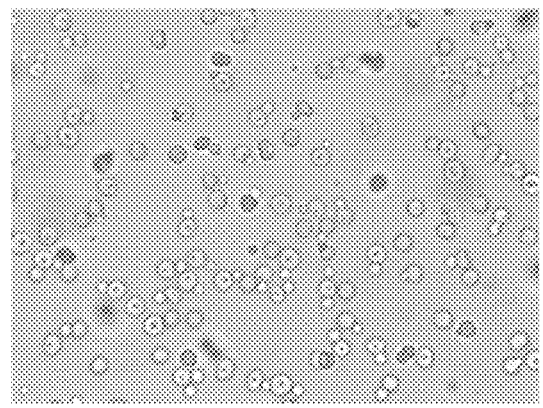
FIG. 11 is an image of spore-shaped erythrocytes photographed by a digital CCD, on which the spore-shaped erythrocytes have vesicles protruded on erythrocyte membranes or are changed into the shape of mold spore, and the erythrocytes are uneven in volume, have deformed shapes like spore and generally have a light chromaticity. The statistical graph of feature parameters of the spore-shaped erythrocytes is as shown in FIG. 12 to FIG. 15, in which dash lines represent normal erythrocytes for the convenience of comparison.
Figure 17:
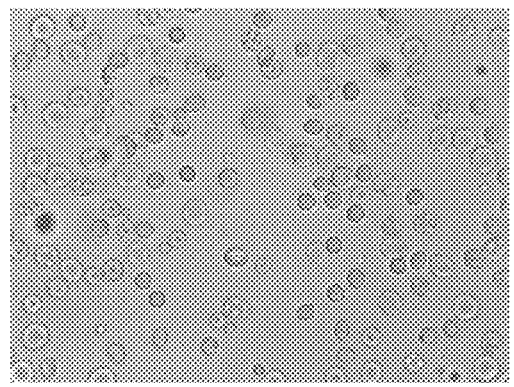
FIG. 17 is an image of erythrocytes uneven in size photographed by a digital CCD. The uneven in size refers that the difference of diameter between erythrocytes is up to twice, and this condition generally appears in various hyperplastic anemia and megaloblastic anemia; the volume is uneven, the chromaticity is lighter and the shape is normal. The statistical graph of feature parameters of the erythrocytes uneven in size is as shown in FIG. 18 to FIG. 22, in which dash lines represent normal erythrocytes for the convenience of comparison.

Step 2: collecting information of an image of the marked area through a camera or a CCD element 2. FIG. 5, FIG. 11 and FIG. 17 are collected images of erythrocytes; for normal erythrocytes, the size is relative uniform, the cell body is normal or relatively big, the haemoglobin is abundant, the cell membrane is complete without spores. The statistical curve of each type of parameters basically has normal distribution (or gaussian distribution) and the distribution area is concentrated relatively.

Step 3: segmenting and positioning cells contained in the image collected at first and then digitizing the segmented image, through an image-digital converter 3, namely, extracting morphological feature parameters of each of the cells, wherein four types of features including size, shape, chromaticity and texture are used to describe each of the cells.

Step 4: inputting the four types of the morphological feature parameters of each of the cells, including size, shape, chromaticity and texture, obtained in Step 3, into a classifier established on the basis of a neural network, and then the classifier isolates erythrocytes from each type of cells. The following table is an example table of part feature parameters of a certain erythrocyte with different types.

The classifier established on the basis of neural network has a feedback process, wherein the feedback process is to refine, classify and compensate feature parameters for a suspected object and a wrongly identified object that are obtained by the classification, and to establish a corresponding mathematical model to train the neural network, wherein the neural network automatically learns and memorizes these refined, classified and compensated feature parameters into a model database, and then to return to the classifier based on the neural network to classify cells.

Step 5: inputting the morphological feature parameters of the erythrocyte isolated in the Step 4 into a feature fusion device established on the basis of fuzzy clustering, and then normalizing the morphological feature parameters by the feature fusion device to obtain one-dimensional feature vectors.

The specific operation of the feature fusion device actually is to perform the calculation, through a feature fusion algorithm based on PCA weight, for each type of feature parameters initially obtained to obtain a normalized feature value.

The feature fusion algorithm based on PCA weight is described below in detail.

Figure 3:
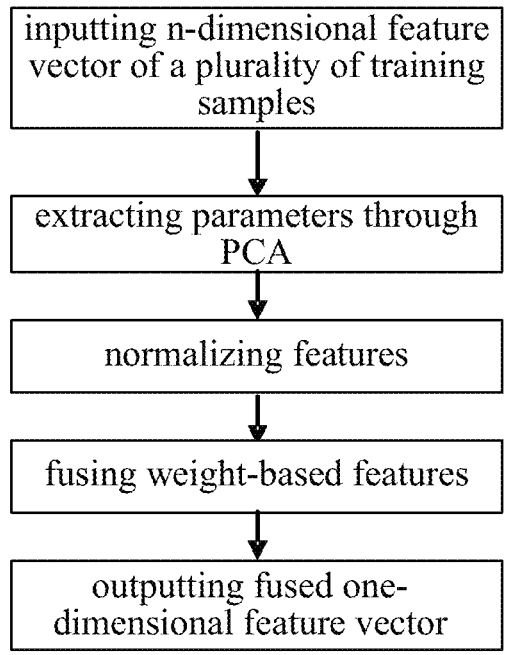
FIG. 3 is a schematic diagram of a feature fusion algorithm based on PCA weight.

1. FIG. 3 is a schematic diagram of the feature fusion algorithm based on PCA weight. First, an n-dimensional feature vector of a training sample is input, wherein the n-dimensional feature vector can be the feature vector of size, shape, texture and chromaticity. Second, the feature extraction is performed through a PCA algorithm, wherein the feature extraction is divided into K-L feature dimension reduction and principle component feature selection. Size feature, shape feature, texture feature and chromaticity feature are selected respectively from the principle component feature vector space which is obtained after the feature extraction. Then, these feature subspaces are subjected to feature vector normalization, and then are subjected to weight fusion in combination with the weight of each dimension of vector, and a corresponding feature value is obtained by the weight fusion

| Erythrocyte Type Area | | Size | | Shape | | Maximum Square Ratio | Chromaticity | | | Texture | | |
|---|---|---|---|---|---|---|---|---|---|---|---|---|
| | | Area | Circumference | Semi-diameter | Circle Ratio | Square Ratio | | Gray Mean | Background Gradient | Area Variance | Inertia | Inverse Difference | Ratio |
| Normal Erythrocyte | | 1091 | 117 | 17 | 1.0015267 | 1.0588236 | 36 | 130 | 9 | 521 | 0.4157527 | 0.8232303 | 0.8828514 |
| Microcyte | | 399 | 69 | 10 | 1.0531354 | 1 | 21 | 158 | 25 | 650 | 1.2656024 | 0.6597968 | 0.4063861 |
| Spherocyte | | 496 | 78 | 11 | 1.0244764 | 1.0434783 | 24 | 181 | 38 | 977 | 1.669383 | 0.6106964 | 0.3515716 |
| Elliptocyte | | 682 | 93 | 12 | 0.9908957 | 1.24 | 31 | 179 | 35 | 1036 | 1.3516667 | 0.6734608 | 0.4525 |
| Ring Erythrocyte | | 865 | 105 | 15 | 0.9859321 | 1.032258 | 32 | 180 | 17 | 631 | 0.7907869 | 0.7289827 | 0.7076136 |
| Acanthocyte | | 580 | 85 | 12 | 1.0087874 | 1.04 | 26 | 158 | 30 | 861 | 1.0678295 | 0.6684108 | 0.5445737 |
| Particle Erythrocyte | | 630 | 90 | 13 | 0.9773836 | 1.0769231 | 28 | 182 | 31 | 850 | 1.1967655 | 0.638814 | 0.5229111 |
| Macrocyte | | 1445 | 137 | 20 | 0.9674671 | 1.05 | 42 | 156 | 11 | 610 | 0.4975755 | 0.8031331 | 0.7855278 |
| Spore-shaped Erythrocyte | | 805 | 111 | 13 | 0.8210307 | 1.4074074 | 38 | 104 | 17 | 765 | 0.8938547 | 0.7223464 | 0.4965084 |
| Stomatocyte | | 1086 | 117 | 17 | 0.9969367 | 1.0882353 | 37 | 209 | 35 | 1312 | 1.0855696 | 0.6759494 | 0.4222785 |
| Tear-drop Erythrocyte | | 862 | 108 | 15 | 0.9286867 | 1.0967742 | 34 | 203 | 17 | 761 | 1.0664928 | 0.7120178 | 0.6219035 |
| Zigzag Erythrocyte | | 1160 | 130 | 18 | 0.862543 | 1.054054 | 39 | 153 | 12 | 652 | 0.6543034 | 0.7550166 | 0.7351403 |
| Shadow Erythrocyte | | 615 | 88 | 13 | 0.9979741 | 1.0384616 | 27 | 157 | 5 | 246 | 0.1868132 | 0.9065934 | 1 |
| Schistocyte | | 825 | 103 | 15 | 0.9772125 | 1 | 30 | 116 | 8 | 456 | 0.3387097 | 0.8387097 | 0.8299731 | for the each feature subspace, and then the feature value is fused to obtain a one-dimensional feature vector.

2. Specifically, the principle of the feature selection algorithm based on PCA is as follows:

the input original feature space is set as $F=\{f_1,f_2,L,f_n\}$, the K-L orthogonal transformation is performed for the F to obtain an orthogonal feature vector space $\{x_1,x_2,L,x_n\}$ with corresponding feature values sorted in a descending order, wherein each feature vector corresponds to a feature value $(\lambda_1,\lambda_2,L,\lambda_n)$ respectively; and a feature vector space is obtained after the dimension reduction through an additive contribution ratio, wherein the additive contribution ratio is as shown in formula (1):

$$e_m = \frac{\sum_{i=1}^{m} \lambda_i}{\sum_{j=1}^{N} \lambda_j} \quad (1)$$

if $e_m > e$ (e is a contribution ratio threshold, $0 < e \le 1$), then the minimum $m(m \le N)$ satisfying conditions is selected. The first m feature vectors, after the dimension reduction, of $\{x_1,x_2,L,x_n\}$ are taken as a feature vector space $V=\{x_1,x_2,L,x_m\}$.

The target of PCA is to extract an m-dimensional principle component feature vector of the original feature space F through the orthogonal vector matrix V, wherein the principle thereof is that, when the original feature vector $\{f_1,f_2,L,f_n\}$ is projected along $x_j$ direction, the PCA makes the energy of obtained $f_1$ maximum; at this moment, $f_1$ is called the first principle component; in the condition of being orthogonal to $x_1$, the projection of the original feature space on $x_2$ makes the energy of $f_2$ maximum; at this moment, $f_2$ is called the second principle component; likewise, a principle component feature space $Y=\{f_1,f_2,L,f_m\}$ can be obtained.

3. Feature normalization feature subspaces $Y_c$, $Y_t$, $Y_s$, $Y_e$ of chromaticity, texture, shape and size are selected respectively from the principle component feature space Y, wherein the expression of the subspaces is as shown in formula (2):

$$\begin{cases} Y_c = \{f_{1c}, f_{2c}, L, f_{kc}\} \\ Y_t = \{f_{1t}, f_{2t}, L, f_{lt}\} \\ Y_s = \{f_{1s}, f_{2s}, L, f_{bs}\} \\ Y_e\{f_{1e}, f_{2e}, L, f_{qe}\} \\ k+l+b+q=m \end{cases} \quad (2)$$

each dimension of feature vector in the feature subspaces of chromaticity, texture, shape and size are normalized respectively, wherein the normalization formula is as shown in formula (3):

$$f_{pni} = \frac{(f_{pmax} - f_{pmin}) \times f_{pi}}{f_{pmax} + f_{pmin}} \quad (3)$$

wherein $f_{pi}$ is the ith feature value in the pth dimension of feature vectors, $f_{pmax}$ and $f_{pmin}$ are the maximum and minimum feature values in the pth dimension of feature vectors. The normalized feature subspaces $Y_{cn}$, $Y_{tn}$, $Y_{sn}$ and $Y_{en}$ are obtained through the formula (3).

4. Feature fusion based on weight function

Since the normalized feature subspaces are extracted from the principle component feature space, it can be known that the contribution capability of each dimension of feature vector is different; thus, the weight occupied is also different. The mean value and standard variance of the feature vectors can be calculated to describe the contribution capability of the feature vector, wherein the calculation formula is as shown in formula (4):

$$\begin{cases} \mu_p = \frac{1}{m}\sum_{i=1}^{m} f_{pni} \\ \sigma_p = \sqrt{\frac{1}{m-1}\sum_{i=1}^{m}(f_{pni}-\mu_p)^2} \end{cases} \quad (4)$$

wherein $\mu_p$ and $\sigma_p$ respectively represent the mean value and standard variance of the pth dimension of vectors.

$|\mu p|$ and $\sigma_p$ can be used to define the identification capability of the following cost function for evaluating features, wherein the evaluation function is as shown in formula (5):

$$J_p = |\mu p|/\sigma_p \quad (5)$$

wherein the bigger the $J_p$ is, the stronger the identification capability of the feature is; and the $J_p$ can be used to represent the weight of each vector. The weight vector corresponding to each vector is $(J_1,J_2,L,J_d)$, wherein d is the number of the feature dimensions of a certain feature subspace. The feature subspace can be fused through matrix transformation to obtain a one-dimensional feature value, wherein the matrix transformation formula is as shown in formula (6):

$$\begin{pmatrix} f_{1n1} & f_{2n1} & L & f_{dn1} \\ f_{2n2} & f_{2n2} & L & f_{dn2} \\ M & M & M & M \\ f_{1nm} & f_{2nm} & L & f_{dnm} \end{pmatrix} \times (J_1, J_2, L, J_d)^T = \begin{pmatrix} a_1 \\ a_2 \\ M \\ a_m \end{pmatrix} \quad (6)$$

The element $\alpha_i$ in $(\alpha_1,\alpha_2,L,\alpha_m)^T$ represents a feature value of the ith training sample corresponding to a certain feature subspace after the dimension reduction, wherein the feature value is normalized to between 0 to 1, and can represent the feature with each type by using different segments.

Through the method above, a one-dimensional feature vector space $(\alpha_c,\alpha_t,\alpha_s,\alpha_e)^T$ of fused normalized chromaticity, texture, shape and size features can be obtained.

Step 6: the values of each type of normalized features of all erythrocytes in each specimen (or each sample) are displayed through an outputting apparatus to obtain a statistical graph of each type of normalized feature parameters.

Step 6.1 the statistical graphs of four types of feature parameters including size, shape, chromaticity and texture of the sample are obtained respectively; the source or type of the erythrocytes in the sample is determined according to direction and degree of deviation obtained by comparing the drawn statistical distribution graph of four types of the feature parameters with the size distribution of normal erythrocyte.

The way of expressing the statistical data diagram of the four types of the feature parameters including size, shape, chromaticity and texture of the sample is not limited, and can be histogram, distribution chart, scattering diagram, curve chart, histogram, area chart, pie chart, scatter diagram, annular chart, radar chart, bubble chart and cylindrical plot, and so on.

Figure 12:
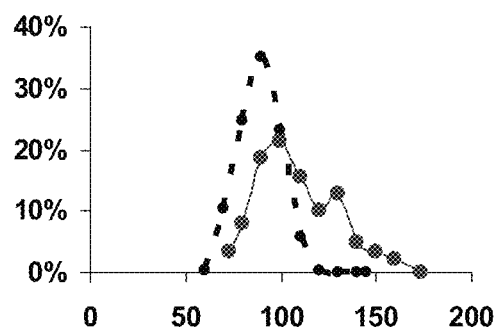
FIG. 12 is a statistical curve chart of the feature parameter Size of spore-shaped erythrocytes, of which, compared with normal erythrocytes, the distribution width a is big and the distribution is not concentrated because the size is uneven and the spore is relatively bigger, and which forms more than one peak at which the frequency value is reduced correspondingly. The distribution width meets a>L; from the curve it can be seen that the width is bigger than the distribution width a of normal erythrocytes, indicating that the erythrocytes are uneven in size; b>D2, indicating that the size of part erythrocytes is relatively bigger.
Figure 18:
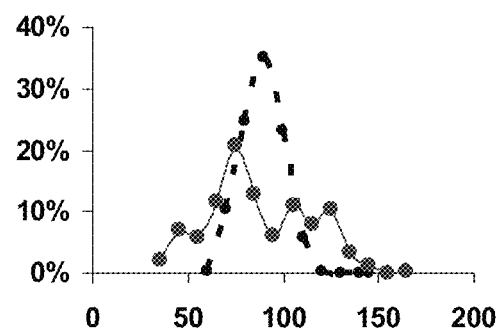
FIG. 18 is a statistical curve chart of the feature parameter Size of erythrocytes uneven in size, of which the distribution width meets a>L; from the curve it can be seen that the width is bigger than the distribution width a of normal erythrocytes, indicating that the erythrocytes are uneven in size; b>D2, indicating that the size of part erythrocytes is relatively bigger.

Step 6.1.1: an erythrocyte size distribution feature curve is drawn by using the fused normalized size feature vector, which are as shown by FIG. 6.1 to FIG. 6.9, FIG. 12 and FIG. 18, wherein the horizontal ordinate represents the value of size and the longitudinal coordinate represents the frequency the corresponding size value appears.

The erythrocyte size feature mainly reflects the condition of size distribution of the erythrocytes in the sample. Left shift of the erythrocyte size distribution feature curve means micro-erythrocyte (or microcytic) change and right shift of the curve means macro-erythrocyte (or macrocytic) change; if the curve has a plurality of peaks, it means some of the erythrocytes is big and some of the erythrocytes is small, and the erythrocytes are uneven in size. If the peak value is small, it means the erythrocyte volume is small; if the peak value is big, it means the erythrocyte volume is big. In case that a plurality of peaks appears, it means the cells with obviously uneven size are mixed; the erythrocyte size distribution condition can be obtained by comparing a plurality of peak values with a reference value. The distribution width of frequency represents the concentration degree of erythrocyte size. The size distribution of the erythrocytes in the sample is compared with the size distribution of normal erythrocytes, and then the source or type of the erythrocytes in the sample is determined according to direction and degree of deviation obtained.

FIG. 6.1 shows a statistical graph of size feature parameter of a urine sample including normal erythrocytes, wherein the statistical graph is shown in the manner of a curve. However, the statistical curve chart of the feature parameter can be expressed in various forms of statistical graphs, such as FIG. 6.2 to FIG. 6.9, all of which are statistical graphs of the size feature parameter of normal erythrocytes.

Figure 4:
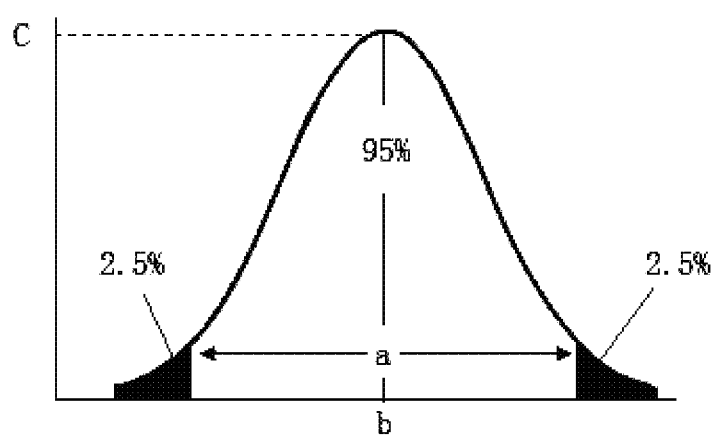
FIG. 4 is a diagram of the distribution width and peak value mentioned in the disclosure.

In order to describe the statistical graph more conveniently, as shown in FIG. 4, $\alpha$ represents the distribution width of the statistical graph. For the statistical curve of the size feature, the evener the erythrocytes are in size, the smaller the distribution width $\alpha$ is. The uneven the erythrocytes are in size, the bigger the distribution width $\alpha$ is. Provided the distribution width threshold is L, when $\alpha>L$, it can be determined that the erythrocytes in the sample are uneven in size, and the system prompts that the sample is suspected to have erythrocytes uneven in size.

b represents an X-axis numerical value corresponding to the distribution peak value of the statistical graph. When the b changes, in the condition that the statistical graph is expressed by a curve, left shift or right shift of the curve occurs. Provided the minimum threshold of the peak value is D1 and the maximum threshold is D2; when $D1 \leq b \leq D2$, the erythrocyte size is in a normal range; when $b<D1$, the curve shifts left and the system prompts the sample is suspected to have micro-erythrocytes; when $b>D2$, the curve shifts right and the system prompts the sample is suspected to have macro-erythrocytes.

FIG. 12 and FIG. 18 are example graph of the statistical graph of the size feature of erythrocytes. FIG. 12 shows the size feature of spore-shaped erythrocytes, wherein the spore-shaped erythrocytes have vesicles protruded from the ectoblast (or membranes) of the spore-shaped erythrocytes or are changed into the shape of mold spore. FIG. 18 shows the size feature of erythrocytes which are uneven in size. The erythrocyte size distribution width of the two figures meets $\alpha>L$; it can be seen from the figures that the width is bigger than the normal erythrocyte size distribution width, indicating that the erythrocytes are uneven in size; $b>D2$, indicating that part erythrocytes are relatively bigger.

Figure 7:
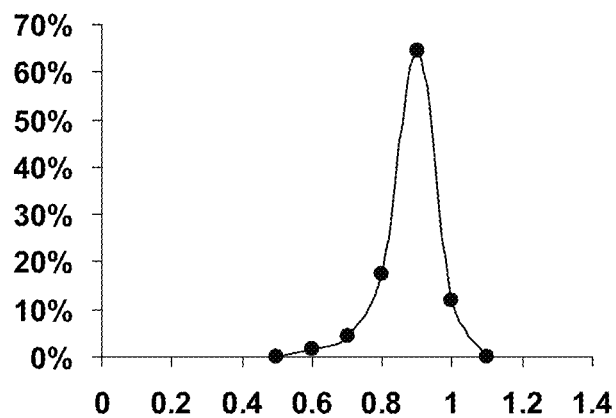
FIG. 7 is a statistical curve chart of the shape feature parameter of normal erythrocytes, of which the distribution is concentrated and the distribution width is small, and on which a frequency value corresponding to the peak value meets C>H (60%)
Figure 13:
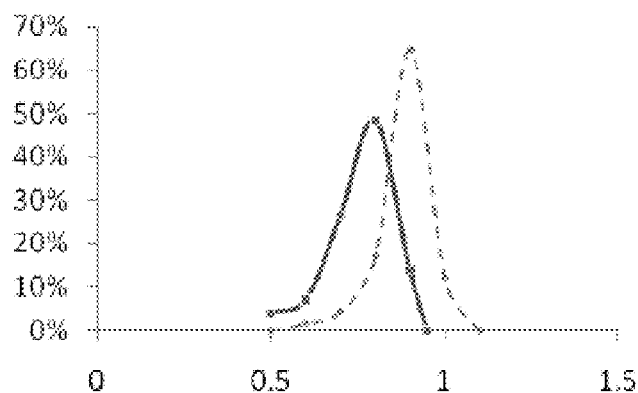
FIG. 13 is a statistical curve chart of the feature parameter Shape of spore-shaped erythrocytes, on which a frequency value C corresponding to the peak value is smaller than that of normal erythrocytes, namely, C<H (60%)
Figure 19:
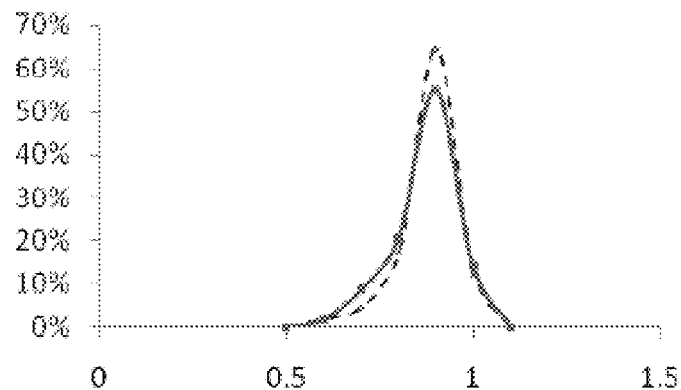
FIG. 19 is a statistical curve chart of the feature parameter Shape of erythrocytes uneven in size, on which a frequency value C corresponding to the peak value is smaller than that of normal erythrocytes, namely, C<H (60%)

Step 6.1.2: an erythrocyte shape distribution feature curve is drawn using the fused normalized shape feature vector, such as FIG. 7, FIG. 13 and FIG. 19, wherein the horizontal ordinate represents the feature value of shape and the longitudinal coordinate represents the frequency the corresponding feature value appears.

The erythrocyte shape distribution feature index mainly reflects the condition of distribution of malformed erythrocytes. Data combination of feature parameters representing shapes (such as circle ratio, square ratio, chord distribution symmetry, convex spore, internally tangent) is used to perform analysis. Normal erythrocytes are in a shape of double-concave disk, and malformed erythrocytes are in a shape of spore, mouth and so on. The source or type of the erythrocytes in the sample is determined according to the change of the erythrocyte shape feature parameter.

FIG. 7 shows a statistical graph of shape feature parameter of a urine sample including normal erythrocytes, wherein the statistical graph is shown in the manner of a curve.

For the statistical curve of the shape feature, more similar the shape of the erythrocyte is with the shape of ideal standard erythrocyte, more concentrated the distribution is, and smaller the distribution width is, and bigger the frequency value C corresponding to the peak value is (0<C<100%). Provided the frequency threshold corresponding to the peak value of the statistical curve of shape feature is H, here, taking H=60% for example, when C<H, the system prompts that the shape of the sample is suspected of being far away from the shape of the ideal erythrocyte.

FIG. 13 and FIG. 19 are example graphs of the statistical graph of the shape feature of erythrocytes. FIG. 13 shows the shape feature of spore-shaped erythrocytes, wherein the spore-shaped erythrocytes have vesicles protruded from the ectoblast (or membranes) of the spore-shaped erythrocytes or are changed into the shape of mold spore. FIG. 19 shows the shape feature of erythrocytes which are uneven in size. The erythrocyte shape distribution width of the two figures do not change a lot, compared with that of normal erythrocytes, while the frequency value C corresponding to the peak value is less than that of normal erythrocytes, namely, C<H.

Figure 8:
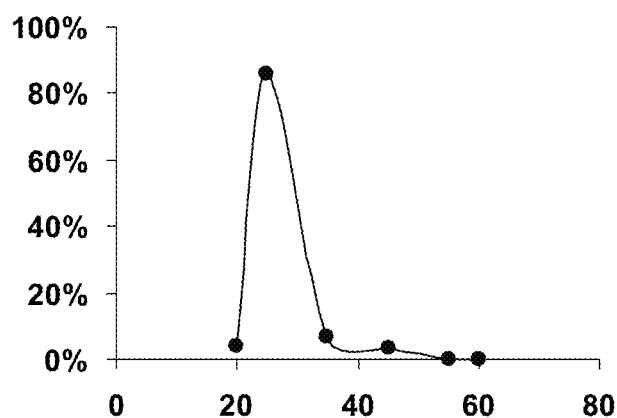
FIG. 8 is a statistical curve chart of the chromaticity feature parameter of normal erythrocytes, which is of a single narrow peak and of which the distribution is concentrated and a frequency value corresponding to the peak value meets C>H (60%)
Figure 14:
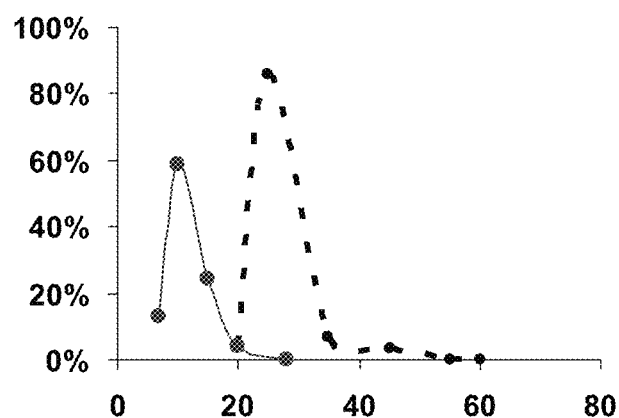
FIG. 14 is a statistical curve chart of the feature parameter Chromaticity of spore-shaped erythrocytes, on which the chromaticity mean value of the spore-shaped erythrocytes is obviously reduced, a frequency value C corresponding to the peak value is smaller than that of normal erythrocytes, namely, C<H, the chromaticity distribution width of the spore-shaped erythrocytes is not big and the cell distribution is uniform and is of a single narrow peak.
Figure 20:
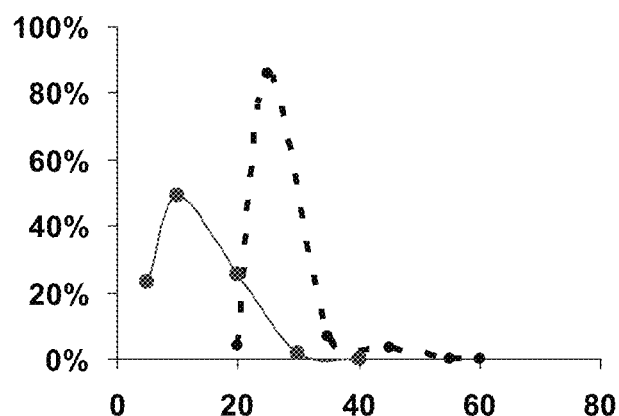
FIG. 20 is a statistical curve chart of the feature parameter Chromaticity of erythrocytes uneven in size, on which the chromaticity mean value of the erythrocytes uneven in size is relatively bigger, a frequency value C corresponding to the peak value is smaller than that of normal erythrocytes, namely, C<H (60%), and the distribution width is obviously increased in the bigger values of chromaticity.

Step 6.1.3: an erythrocyte chromaticity distribution feature curve is drawn using the fused normalized chromaticity feature vector, such as FIG. 8, FIG. 14 and FIG. 20, wherein the horizontal ordinate represents the chromaticity value and the longitudinal coordinate represents the frequency the corresponding chromaticity value appears.

The erythrocyte chromaticity distribution feature mainly reflects the condition of loss of erythrocyte haemoglobin. Data combination of feature parameters representing chromaticity (such as tone, saturation and so) is used to perform analysis. The source or type of the erythrocytes in the sample is determined according to direction and degree of deviation obtained by comparing the erythrocyte chromaticity with normal erythrocyte chromaticity.

After erythrocytes lose haemoglobin, the chromaticity of the erythrocyte will become lighter; in this condition, the curve of the frequency histogram of the erythrocyte chromaticity distribution feature shifts left and the peak value becomes smaller. The erythrocytes lose water easily in hypertonic urine to form shrinkage erythrocytes, and the chromaticity becomes darker; in this condition, the curve of the frequency histogram of chromaticity shifts right and the peak value becomes bigger. These conditions are not included in the scope of abnormality, and identification and judgment are needed.

FIG. 8 shows a statistical graph of chromaticity feature parameter of a urine sample including normal erythrocytes; here, the statistical graph is shown in the manner of a curve. For the statistical curve of the chromaticity feature, more similar the chromaticity of the erythrocytes is with that of normal erythrocytes, more concentrated the distribution is, and bigger the frequency value C corresponding to the peak value is (0<C<100%). Provided the frequency threshold corresponding to the peak value of the statistical curve of chromaticity feature is H, here, taking H=60% for example, when C<H, the system prompts that the chromaticity of a majority of the erythrocytes in the sample are far away from the chromaticity of ideal erythrocytes. For the statistical curve of the chromaticity feature, the distribution width is smaller when the erythrocyte chromaticity distribution is closer.

In FIG. 4, b represents an X-axis numerical value corresponding to the distribution peak value of the statistical graph; when the b changes, in the condition that the statistical graph is expressed by a curve, the left shift or right shift of curve occurs, that is, the chromaticity of erythrocytes changes. Darker the chromaticity is, Bigger the b is. Lighter the chromaticity is, Smaller the b is. Provided the minimum threshold of the X-axis corresponding to the peak value is S1 and the maximum threshold is S2. When S1<b<S2, the chromaticity of erythrocytes is in a normal range; when b<S1, the curve shifts left, indicating that the chromaticity of cells is relatively lower; when b>S2, the curve shifts right, indicating that the chromaticity of cells is relatively higher.

FIG. 14 and FIG. 20 are example graphs of the statistical graph of the chromaticity feature of erythrocytes. Dash line represents the chromaticity of the normal erythrocyte and is of a single narrow peak, indicating that the chromaticity of cells is very even and no cytoplasm is lost. The chromaticity of erythrocytes is relevant to the content of haemoglobins. FIG. 14 shows the chromaticity feature of spore-shaped erythrocytes. FIG. 20 shows the chromaticity feature of erythrocytes which are uneven in size. The mean values of the chromaticity of the erythrocyte of the two figures both change, compared with that of normal erythrocytes. The mean value of the chromaticity of the spore-shaped erythrocytes in FIG. 14 is obviously reduced. The mean value of the chromaticity of the erythrocytes which are uneven in size in FIG. 20 is relatively higher. Both the frequency values C corresponding to the peak value are obviously less than that of normal erythrocytes, namely, C<H. The chromaticity distribution width of the spore-shaped erythrocytes in FIG. 14 does not change a lot, and the cell distribution is even and with a single narrow peak. The distribution width of the erythrocytes which are uneven in size in FIG. 20 is obviously increased along the direction where the values of chromaticity are relatively bigger.

Figure 9:
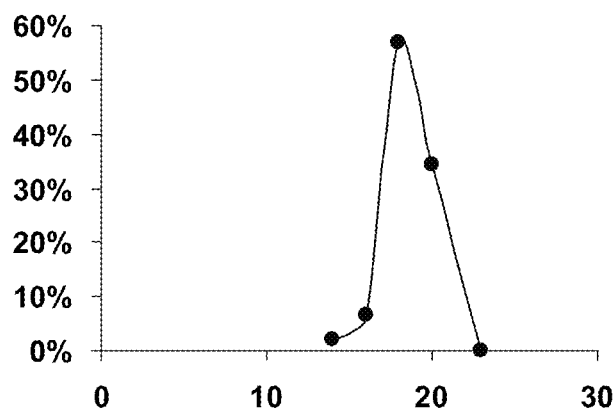
FIG. 9 is a statistical curve chart of the texture feature parameter of normal erythrocytes, on which a numerical value b on X-axis corresponding to the peak value is in a normal range, namely, W1<b<W2.
Figure 15:
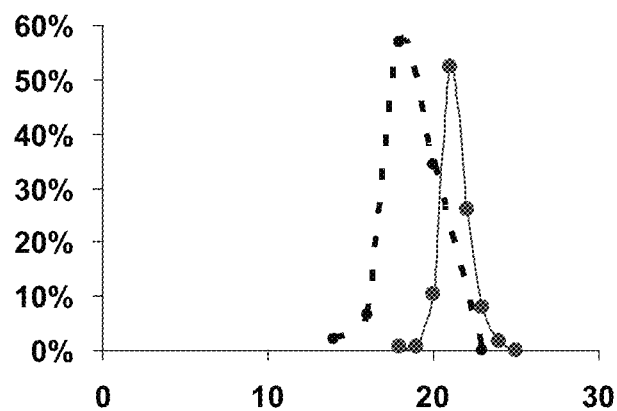
FIG. 15 is a statistical curve chart of the feature parameter Texture of spore-shaped erythrocytes, on which the texture of the spore-shaped erythrocytes is more complex compared with normal erythrocytes, and a numerical value b on X-axis corresponding to the peak value is relatively bigger, namely, b>W2.
Figure 21:
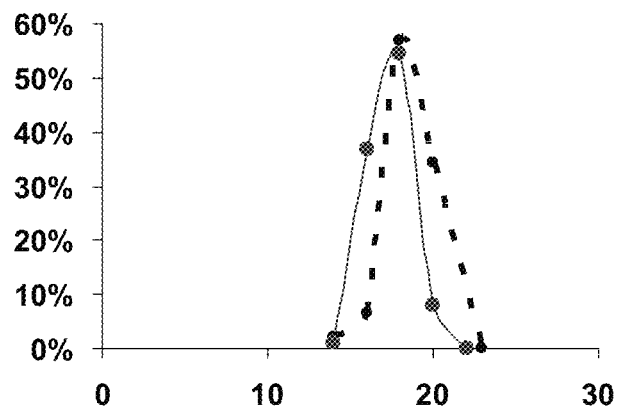
FIG. 21 is a statistical curve chart of the feature parameter Texture of erythrocytes uneven in size.

Step 6.1.4: an erythrocyte texture distribution feature curve is drawn using the fused normalized texture feature vector, as shown in FIG. 9, FIG. 15 and FIG. 21, wherein the horizontal ordinate represents the value of texture and the longitudinal coordinate represents the frequency the corresponding texture value appears.

The erythrocyte texture distribution feature is analyzed by using data combination of feature parameters which represent colour gradient of the central area (for example, expansion of central pale area, disappearance of central pale area, chromaticity enhancement of central area and so on) of the erythrocyte and represent texture. The source or type of the erythrocytes in the sample is determined according to direction and degree of deviation obtained by comparing the erythrocyte texture with normal erythrocyte texture.

FIG. 9 shows a statistical graph of texture feature parameter of a urine sample including normal erythrocytes; here, the statistical graph is shown in the manner of a curve. For the statistical curve of the texture feature, when the texture of the erythrocyte is more abundant, the texture value is bigger. As shown in FIG. 4, α represents the distribution width of the statistical graph. Smaller the difference in the change of the texture between the cells in the sample is, smaller the distribution width α of the statistical graph is; the bigger the difference in the change of texture between the cells is, bigger the distribution width α of the statistical graph is.

In FIG. 4, b represents an X-axis numerical value corresponding to the distribution peak value of the statistical graph; when the b changes, in the condition that the statistical graph is expressed by a curve, the curve shifts left or shifts right, that is, the intensity of the texture of erythrocytes changes. More intense the texture is, greater the energy thereof is, and bigger the b is; shallower the texture is, smaller the b is. Provided the minimum threshold of the X-axis corresponding to the peak value is W1 and the maximum threshold is W2; when W1<b<W2, the texture of erythrocytes is in a normal range; when b<W1, it is indicated that the texture of the sample is weak and the curve shifts left; when b>W2, it is indicated that the texture of the sample is relatively thick and the curve shifts right.

FIG. 15 shows the texture feature of spore-shaped erythrocytes. FIG. 21 shows the texture feature of erythrocytes which are uneven in size. The mean values of the texture of erythrocytes of the two figures both change, compared with that of normal erythrocytes.

Step 6.2: the normalized feature vectors of more than two types of above are combined with each other and the comprehensive analysis is performed using a statistical method to obtain a multi-parameter analysis chart.

Taking that the comprehensive analysis is performed for the combination of two types of the normalized feature vectors including size and chromaticity of erythrocytes for example, as shown in FIG. 10, FIG. 16, FIG. 22 and FIG. 23; a scatter diagram is drawn with the erythrocyte size value as the horizontal ordinate and the corresponding erythrocyte chromaticity value as the longitudinal coordinate.

Figure 10:
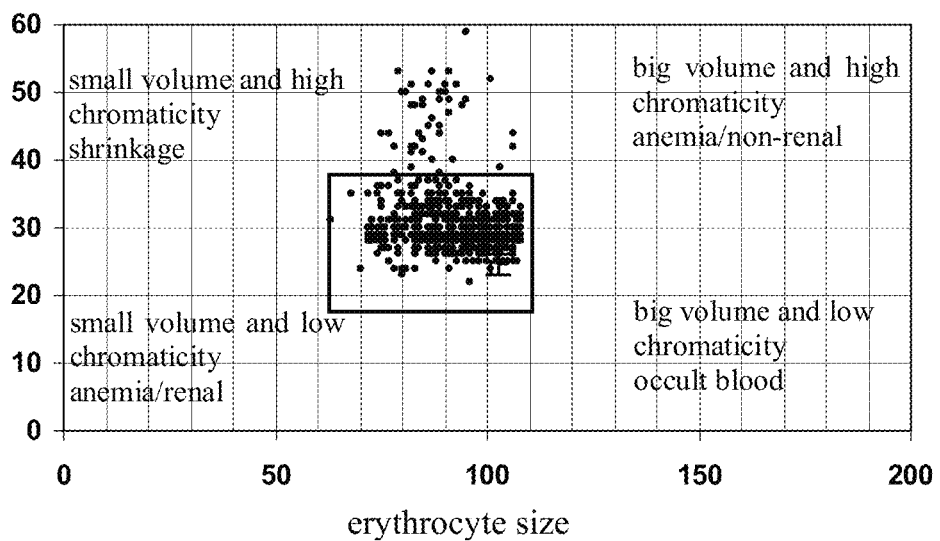
FIG. 10 is a scatter diagram for the comprehensive analysis of size and chromaticity feature parameters of normal erythrocytes, on which normal erythrocytes are concentrated in a range of 75<X<125 and 20<Y<40.

FIG. 10 is a diagram for the comprehensive analysis of size and chromaticity of normal erythrocytes, wherein the normal erythrocytes are concentrated in a range of 75<X<125 and 20<Y<40.

Figure 16:
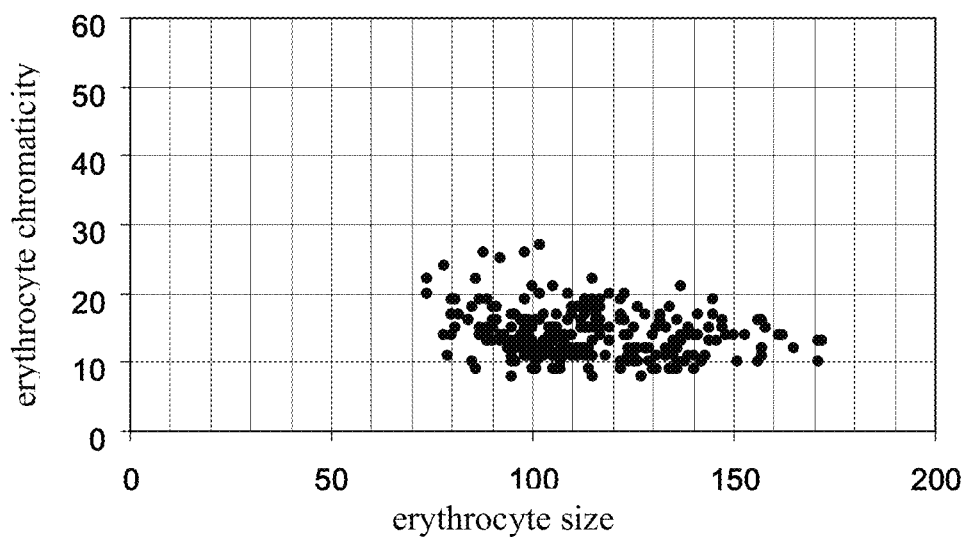
FIG. 16 is a scatter diagram for the comprehensive analysis of feature parameters Size and Chromaticity of spore-shaped erythrocytes, on which the chromaticity value of the erythrocytes is obviously lower, and the size range of the erythrocytes is expanded, mainly distributed in a range of 80<X<160.
Figure 22:
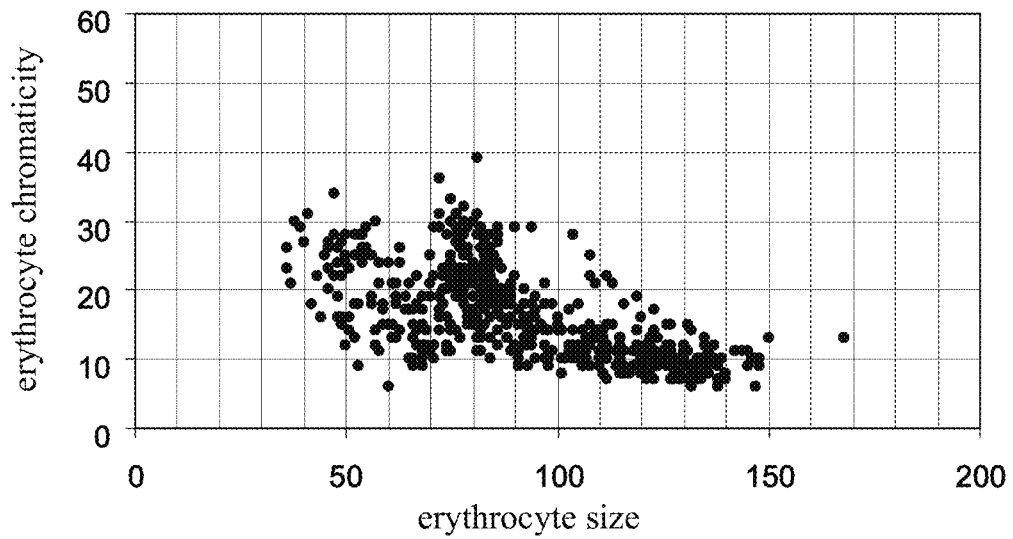
FIG. 22 is a scatter diagram for the comprehensive analysis of feature parameters Size and Chromaticity of erythrocytes uneven in size, on which the chromaticity and size of the erythrocytes are distributed in a big range, namely, 5<X<30 and 40<Y<150.

FIG. 16 is a diagram for the comprehensive analysis of size and chromaticity of spore-shaped erythrocytes, wherein the chromaticity of the erythrocytes is obviously lower, and the size range of the erythrocytes is expanded, mainly distributed in a range of 80<X<160. FIG. 22 is a diagram for the comprehensive analysis of erythrocytes which are uneven in size, wherein the chromaticity and size of the erythrocytes are distributed in a relatively bigger range, e.g., 5<X<30 and 40<Y<150.

The same result presented by using this device to analyze erythrocytes has different clinical meanings in different kind of samples, for example, if the erythrocytes with small volume and low pigment appear in a sample, the result analyzed by this device is that a single erythrocyte has a small volume and a low chromaticity, and for total erythrocytes morphological feature parameters, a morphological analysis graph, which takes a parameter combination representing size as a horizontal coordinate and takes feature parameter data representing chromaticity as a longitudinal coordinate, is adopted to express that the width of an erythrocyte distribution increases and the erythrocyte distribution shifts left, and the area of the erythrocyte distribution shifts downwardly, that is, the total erythrocytes morphological feature parameters are expressed as an erythrocyte morphological distribution chart with dispersion toward left and descending downwardly, wherein a type of anaemia is prompted if this type of the graph appears in a blood sample, whereas it means that the erythrocytes in the sample come from renal erythrocytes if this type of the graph appears in a urine sample and occupies a certain proportion.

Figure 23:
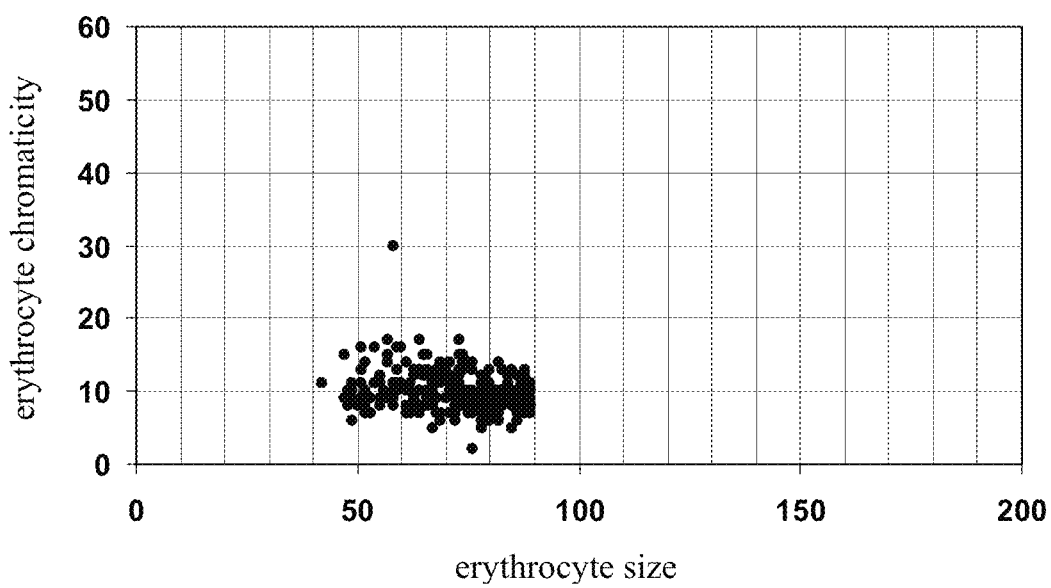
FIG. 23 is a scatter diagram for the comprehensive analysis of feature parameters of small-volume hypochromic erythrocytes (anaemia or renal)

As shown by FIG. 23, when P % (50≤P≤100) erythrocytes in the blood sample are distributed in a region of X<75 and Y<20, the system prompts that the sample is suspected of anaemia; when P % (50≤P≤100) erythrocytes in the urine sample are distributed in a region of X<75 and Y<20, the system prompts that the sample is suspected of nephropathy.

Step 7: a statistical processing is performed for the each type of erythrocytes according to the proportion of each type of erythrocytes to total erythrocytes in the sample, and the result of the statistical processing is expressed in the form of graph or data to analyze and identify the erythrocyte in the sample.

Figure 24:
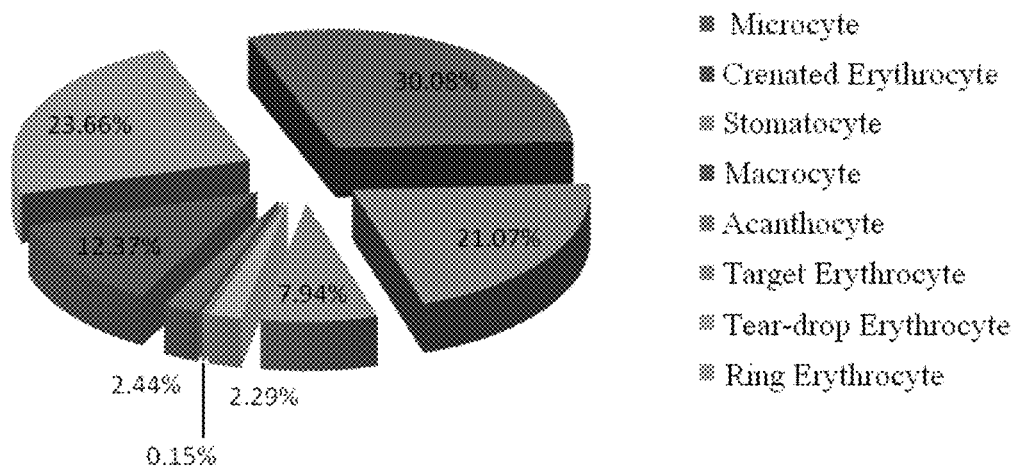
FIG. 24 is a statistical graph of the proportion of each cell to total erythrocytes in a sample.

As shown in FIG. 24, the proportion of each type of erythrocytes to total erythrocytes in the sample is obtained by performing identification and classification counting on the cells in the sample. In the condition that the expression is in the form of graph or data, it is convenient for an operator to judge the condition of the sample based on the data. Here, the expression in the form of a statistical pie chart is taken for example.

Step 7: according to a normalized one-dimensional morphological feature vector of each type of erythrocytes in the sample, through giving a feature value threshold, calculating the proportion of a data combination of one morphological feature parameter (or one type of morphological feature parameters) of the erythrocytes whose the morphological feature vector is higher or lower than the threshold to a data combination of the same morphological feature parameter (or the same type of morphological feature parameters) of total erythrocytes in the sample and the result is expressed in the form of graph or data after performing statistical processing.

Figure 25:
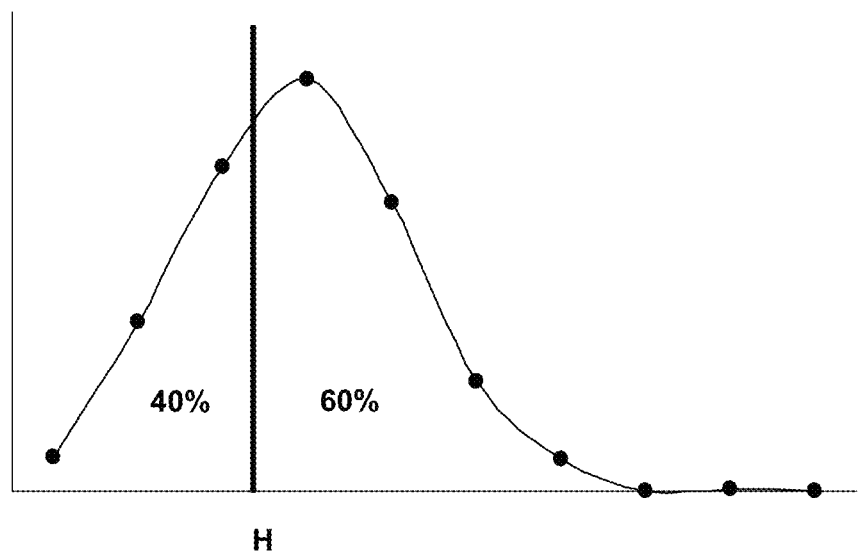
FIG. 25 is a statistical graph of the feature parameter Chromaticity of a sample.
Figure 26:
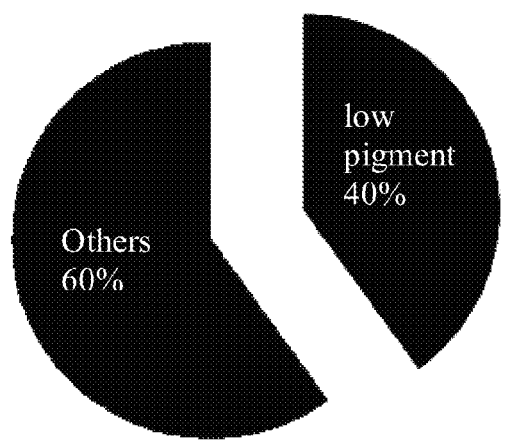
FIG. 26 is another expression form of FIG. 24.

FIG. 25 is a statistical graph of chromaticity feature parameter of a sample. In FIG. 25, a fused normalized chromaticity one-dimensional feature vector is used to judge erythrocytes with low pigment (or hypochromic), wherein the given threshold of chromaticity is set to be H, wherein the percentage of the erythrocytes with chromaticity lower than the threshold H in the sample is 40%; that is to say, the erythrocytes with low pigment (or hypochromic) in the sample is 40% of the total number of erythrocytes. FIG. 26 is another expression form of FIG. 25.

The expression form of graph or data above is displayed on an output device, for relevant staff reference. The output device can be a display window on a device for performing morphological analysis for erythrocytes in the disclosure, also can be a display connected with the device for performing morphological analysis for erythrocytes, or a display connected with network for remote diagnosis. The graph or data above also can be printed out for a doctor to perform analysis.

Figure 27:
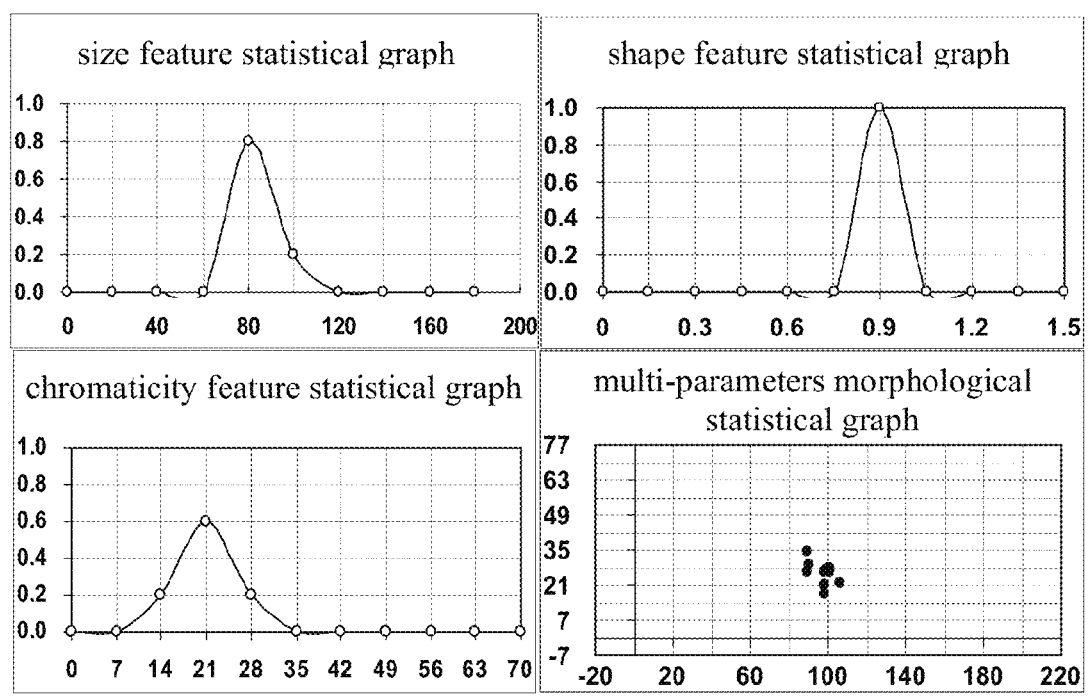
FIG. 27 is a statistical graph expressed by an arrangement of multiple charts.

The statistical graph can be expressed by an arrangement of multiple charts, as shown in FIG. 27. The statistical graph also can be displayed in a single chart.

In addition, the sample involved in the disclosure can be a urine sample and a blood sample. It should be noted that the blood sample is not subjected to a smear process, but is analyzed after the blood sample is diluted by certain multiples; in this way, the damage to part cells in the sample caused by smear is avoided. The disclosure requires a fresh sample; it is best to perform examination within two hours after the sample is obtained; the sample does not need to be dyed but is not limited to be not dyed; in this way, no expensive reagent is required to be used in the examination process; therefore, the disclosure is economical, free of pollution and is good for environment protection.

What is claimed is:
1. A device for performing morphological analysis for erythrocytes, comprising:
   a: an automatic microscope, wherein a low-power objective lens of the automatic microscope is configured to scan a sample in a set area and to mark a found target area, and meanwhile a high-power objective lens of the automatic microscope is configured to scan the marked area;
   b: a camera or a Charge Coupled Device (CCD) element, which is configured to collect information of an image of the marked area;
   c: an image-digital converter for analyzing and processing the image, wherein the image-digital converter is configured to segment and position cells contained in the image collected at first, and then to digitize the segmented image to extract four types, including size, shape, chromaticity and texture, of morphological feature parameters of each of the cells;
   d: a classifier established on the basis of a neural network, wherein the classifier is configured to classify the cells according to the four types, including size, shape, chromaticity and texture, of the morphological feature parameters of each of the cells, obtained in the above step, so as to isolate erythrocytes from each type of the cells;
   e: a feature fusion device established on the basis of fuzzy clustering, wherein the feature fusion device is configured to perform normalized dimension reduction on the four types, including size, shape, chromaticity and texture, of multi-dimensional morphological feature parameters of the erythrocytes, which are isolated in the above step, to obtain four feature values of size, shape, chromaticity and texture, and then to perform statistical calculation and statistical graphic expression respectively according to size, shape, chromaticity and texture features of all erythrocytes in a specimen to provide real objective basis for analyzing type and source of the erythrocytes in the sample;
   f: an output apparatus, which is configured to intuitively display a detection result; and
   g: a control unit, which is connected to the automatic microscope, the camera or CCD element, the image-digital converter and the output apparatus respectively to control actions of the automatic microscope, the camera or CCD element, the image-digital converter and the output apparatus;
   wherein a method for performing morphological analysis for the erythrocytes in the sample comprises:
      performing identification and classification counting by referring to different morphological feature parameter data of each type of erythrocytes clinically confirmed and representing different meanings, and then performing statistical processing according to the proportion of a data combination of a morphological feature parameter of the morphological feature parameters of each type of erythrocytes to a data combination of the same morphological feature parameter of the morphological feature parameters of total erythrocytes in the sample and finally to perform expression in the form of graph or data;
      or,
      comprehensively analyzing a combination of more than two types of morphological feature parameters of each type of the erythrocytes in the sample according to a statistical method to obtain a multi-parameter analysis result of each type of the erythrocytes in the sample, and determining the morphological change of the erythrocytes according to the change of the parameter and intuitively expressing the type of the morphological change of the erythrocytes in the sample through graph and data.

2. The device for performing morphological analysis for erythrocytes according to claim 1, wherein the output apparatus expresses data combination of feature parameters, which represent colour gradient and texture of a central area of the erythrocytes, owned by each type of the erythrocytes, and a method for analyzing and identifying the erythrocytes in the sample comprises determining the source or type of the erythrocytes in the sample according to feature change in the central area of the erythrocytes.

3. The device for performing morphological analysis for erythrocytes according to claim 1, wherein one same result presented by using the device to analyze erythrocytes has different clinical meanings in different kind of samples, if erythrocytes with small volume and low pigment appear in a sample, the result analyzed by the device is that a single erythrocyte has a small volume and a low chromaticity, and for total erythrocytes morphological feature parameters, a morphological analysis graph, which takes a parameter combination representing size as a horizontal coordinate and takes feature parameter data representing chromaticity as a longitudinal coordinate, is adopted to express left shift of the width of the erythrocyte distribution increases and the erythrocyte distribution shifts left, the area of the erythrocyte distribution shifts downwardly, that is, the total erythrocytes morphological feature parameters are expressed as an erythrocyte morphological distribution chart with dispersion toward left and descending downwardly, wherein a type of anaemia is prompted if this type of the graph appears in a blood sample, whereas it means the erythrocytes in the sample come from renal erythrocytes if this type of the graph appears in a urine sample and occupies a certain proportion; if erythrocytes with large volume and high pigment appear in a sample, the result analyzed by the device is that a single erythrocyte has a large volume and a high chromaticity, and for total erythrocytes morphological feature parameters, a morphological analysis graph, which takes a parameter combination representing size as a horizontal coordinate and takes feature parameter data representing chromaticity as a longitudinal coordinate, is adopted to express that the width of an erythrocyte distribution increases and the erythrocyte distribution shifts right and an area of the erythrocyte distribution shifts upwardly, that is, the total erythrocytes morphological feature parameters is expressed as an erythrocyte morphological distribution chart with dispersion toward right and ascending upwardly, wherein another type of anaemia is prompted if this type of the graph appears in a blood sample, whereas it means that the erythrocytes in the sample come from non-renal erythrocytes if this type of the graph appears in a urine sample and occupies a certain proportion.

4. A method for performing morphological analysis for erythrocytes, comprising the following steps:
Step 1: scanning a sample in a set area and marking a found target area through a low-power objective lens of an automatic microscope and meanwhile scanning the sample in the marked area through a high-power objective lens of the automatic microscope;
Step 2: collecting information of an image of the sample in the marked area through a camera or a CCD element;
Step 3: segmenting and positioning cells contained in the image collected and then digitizing the segmented image to extract morphological feature parameters of each of the cells through an image-digital converter, wherein four types of features including size, shape, chromaticity and texture are used to describe each of the cells;
Step 4: inputting the four types, including size, shape, chromaticity and texture, of the morphological feature parameters of each of the cells, which are obtained in the above step, into a classifier established on the basis of a neural network, and then isolating erythrocytes from each type of the cells;
Step 5: inputting the four types, including size, shape, chromaticity and texture, of the morphological feature parameters of the erythrocytes, which are isolated in the Step 4, into a feature fusion device established on the basis of fuzzy clustering, and then normalizing each type of multi-dimensional morphological feature parameters by the feature fusion device to obtain a one-dimensional feature vector; and
Step 6: displaying each type of normalized feature values of all erythrocytes in each specimen through an outputting apparatus to obtain a statistical graph of each type of normalized feature parameters;
wherein the method further comprising Step 7: performing statistical processing according to the proportion of each type of the erythrocytes to total of the erythrocytes in the sample and performing expression in the form of graph or data to analyze and identify the erythrocytes in the sample.

5. The method for performing morphological analysis for erythrocytes according to claim 4, further including Step 8: for each type of normalized morphological feature vectors, through giving a feature value threshold, calculating the proportion of a data combination of one morphological feature parameter of the morphological feature parameters of the erythrocytes whose the normalized morphological feature vectors are higher or lower than the threshold to a data combination of the same morphological feature parameter of the morphological feature parameters of total erythrocytes in the sample, and performing expression in the form of graph or data after performing statistical processing so as to provide objective basis for the analysis and identification of the erythrocytes in the sample.

6. The method for performing morphological analysis for erythrocytes according to claim 4, wherein the classifier established on the basis of the neural network includes a feedback process which is to refine, classify and compensate feature parameters for a suspected object and a wrongly identified object that are classified out, and to establish a corresponding mathematical model to train the neural network, wherein the neural network automatically learns and memorizes these refined, classified and compensated feature parameters into a model database, and then to return to the classifier based on the neural network to classify the cells.

7. The method for performing morphological analysis for erythrocytes according to claim 4, wherein the normalized size feature vector obtained in Step 6 expresses data combination of feature parameters, representing size, owned by each type of the erythrocytes; the method for analyzing and identifying the erythrocytes in the sample determines the source or type of the erythrocytes in the sample according to direction and degree of deviation obtained by comparing the size distribution of the erythrocytes with the size distribution of normal erythrocytes.

8. The method for performing morphological analysis for erythrocytes according to claim 4, wherein the normalized shape feature vector obtained in Step 6 expresses data combination of feature parameters, representing shape, owned by each type of the erythrocytes; the method for analyzing and identifying the erythrocytes in the sample determines the source or type of the erythrocytes in the sample according to the change of the erythrocyte shape feature parameter.

9. The method for performing morphological analysis for erythrocytes according to claim 4, wherein the normalized chromaticity feature vector obtained in Step 6 expresses data combination of feature parameters, representing chromaticity, owned by each type of the erythrocytes; the method for analyzing and identifying the erythrocytes in the sample determines the source or type of the erythrocytes in the sample according to direction and degree of deviation obtained by comparing the erythrocyte chromaticity with normal erythrocyte chromaticity.

10. The method for performing morphological analysis for erythrocytes according to claim 4, wherein the normalized texture feature vector obtained in Step 6 expresses a data combination of feature parameters, representing texture, owned by each type of the erythrocytes; the method for analyzing and identifying the erythrocytes in the sample determines the source or type of the erythrocytes in the sample according to the change of the erythrocyte texture feature parameter.

11. The method for performing morphological analysis for erythrocytes according to claim 4, wherein any one of the following is adopted separately or at least two of the following are adopted comprehensively for the analysis and identification of the erythrocytes in the sample:

the normalized size feature vector obtained in Step 6 expresses data combination of feature parameters, representing size, owned by each type of the erythrocytes; the method for analyzing and identifying the erythrocytes in the sample determines the source or type of the erythrocytes in the sample according to direction and degree of deviation obtained by comparing the size distribution of the erythrocytes with the size distribution of normal erythrocytes;

the normalized shape feature vector obtained in Step 6 expresses data combination of feature parameters, representing shape, owned by each type of the erythrocytes; the method for analyzing and identifying the erythrocytes in the sample determines the source or type of the erythrocytes in the sample according to the change of the erythrocyte shape feature parameter;

the normalized chromaticity feature vector obtained in Step 6 expresses data combination of feature parameters, representing chromaticity, owned by each type of the erythrocytes; the method for analyzing and identifying the erythrocytes in the sample determines the source or type of the erythrocytes in the sample according to direction and degree of deviation obtained by comparing the erythrocyte chromaticity with normal erythrocyte chromaticity;

the normalized texture feature vector obtained in Step 6 expresses a data combination of feature parameters, representing texture, owned by each type of the erythrocytes; the method for analyzing and identifying the erythrocytes in the sample determines the source or type of the erythrocytes in the sample according to the change of the erythrocyte texture feature parameter.

* * * * *